(12) United States Patent
Zheng et al.

(10) Patent No.: US 8,900,146 B2
(45) Date of Patent: Dec. 2, 2014

(54) THREE-DIMENSIONAL (3D) ULTRASOUND IMAGING SYSTEM FOR ASSESSING SCOLIOSIS

(75) Inventors: Yongping Zheng, Kowloon (HK); James Chung Wai Cheung, Hong Kong (HK)

(73) Assignee: The Hong Kong Polytechnic University (CN)

( * ) Notice: Subject to any disclaimer, the term of this patent is extended or adjusted under 35 U.S.C. 154(b) by 1040 days.

(21) Appl. No.: 12/509,705

(22) Filed: Jul. 27, 2009

(65) Prior Publication Data
US 2011/0021914 A1    Jan. 27, 2011

(51) Int. Cl.
| | | |
|---|---|---|
| *A61B 8/00* | (2006.01) | |
| *A61B 5/103* | (2006.01) | |
| *A61B 5/107* | (2006.01) | |
| *A61B 8/08* | (2006.01) | |
| *G06T 7/00* | (2006.01) | |
| *A61B 5/00* | (2006.01) | |

(52) U.S. Cl.
CPC .............. *A61B 5/103* (2013.01); *A61B 8/4245* (2013.01); *G06T 2207/10016* (2013.01); *A61B 5/1071* (2013.01); *G06T 2207/30012* (2013.01); *A61B 8/483* (2013.01); *G06T 2207/10136* (2013.01); *A61B 8/0875* (2013.01); *G06T 7/0012* (2013.01); *A61B 5/4561* (2013.01); *G06T 2207/20096* (2013.01); *G06K 2209/055* (2013.01); *G06T 2200/04* (2013.01)
USPC ......................................... 600/443; 382/128

(58) Field of Classification Search
USPC ........................................ 600/443; 382/128
See application file for complete search history.

(56) References Cited

U.S. PATENT DOCUMENTS

| | | | |
|---|---|---|---|
| 4,437,468 A | 3/1984 | Sorenson et al. | |
| 4,457,311 A | 7/1984 | Sorenson et al. | |
| 4,458,689 A | 7/1984 | Sorenson et al. | |
| 4,476,873 A | 10/1984 | Sorenson et al. | |
| 4,489,729 A | 12/1984 | Sorenson et al. | |
| 5,709,206 A * | 1/1998 | Teboul | .......................... 600/437 |
| 6,058,527 A * | 5/2000 | Charpin | ..................... 5/81.1 RP |
| 6,193,657 B1 | 2/2001 | Drapkin | |

(Continued)

FOREIGN PATENT DOCUMENTS

| | | |
|---|---|---|
| CN | 1973776 A | 6/2007 |
| CN | 100998511 A | 7/2007 |
| WO | WO-00/63719 A1 | 10/2000 |

OTHER PUBLICATIONS

"International Application Serial No. PCT/CN2010/075287, International Search Report mailed Nov. 4, 2010", 3 pgs.

(Continued)

*Primary Examiner* — Jonathan Cwern
(74) *Attorney, Agent, or Firm* — Schwegman, Lundberg & Woessner, P.A.

(57) ABSTRACT

A three-dimensional (3D) ultrasound imaging system (10) for assessing scoliosis, the system (10) comprising: an ultrasound scanner (11) to capture ultrasound images; a spatial sensor (13) to record the position and orientation of the captured ultrasound images; and a software module (21) to mark features of vertebra in the captured ultrasound images, and the marked features (41) are connected with lines (42) in order to calculate angles and distances between the marked features (41) for the calculation of the Cobb angle and spinal rotation angle based on the calculated angles and distances; wherein the marked features (41) are a reflection of the surfaces of the vertebra.

25 Claims, 12 Drawing Sheets

(56) References Cited

U.S. PATENT DOCUMENTS

| | | |
|---|---|---|
| 6,668,083 B1 * | 12/2003 | Verdonck et al. ............. 382/203 |
| 2002/0133098 A1 * | 9/2002 | Shechtman et al. ........... 600/594 |
| 2005/0070783 A1 * | 3/2005 | Yanagita ....................... 600/407 |
| 2005/0213849 A1 * | 9/2005 | Kreang-Arekul et al. .... 382/284 |
| 2007/0276243 A1 * | 11/2007 | Gerard et al. ................. 600/440 |

OTHER PUBLICATIONS

"Chinese Application Serial No. 201080040696.0, Office Action mailed Dec. 28, 2012", 8 pgs.

* cited by examiner

THREE-DIMENSIONAL (3D) ULTRASOUND IMAGING SYSTEM FOR ASSESSING SCOLIOSIS

TECHNICAL FIELD

The invention concerns a three-dimensional (3D) ultrasound imaging system for assessing scoliosis.

BACKGROUND OF THE INVENTION

Scoliosis is a medical condition in which the spine of a person is curved from side to side, and may also be rotated. X-ray assessment is commonly used to determine scoliosis. Other techniques for determining scoliosis include Moire-fringe mapping, raster-based systems, 360° torso profile scanning and stereo-photogrammetric systems.

Measurement of the Cobb angle based on X-ray images is the primary method for scoliosis assessment. Many radiographs of scoliosis patients must be taken during treatment or over a monitoring period which leads to high doses of exposure to radiation. Therefore, this technique is not suitable for children and adolescents.

Also, the interpretation of results from radiographs is highly subjective. It may be difficult to identify oblique projections of a twisting spine and the Cobb angle largely varies depending on the angle of the X-ray beam to the patient. Also, intra-rater and inter-rate variability of 3 to 5° and 6 to 7° respectively have been reported in the calculation of the Cobb angle. Further, rotation of the spine can affect the degree of the Cobb angle, however, the degree of rotation cannot be considered because no rotation information can be obtained by a standard chest X-ray. X-ray examination requires a special room and trained specialists to operate the X-ray equipment. These factors limit the use of X-ray for scoliosis examination.

Traditionally, scoliosis screening has relied on the Adam's forward blend test (FBT). The FBT does not provide a quantitative description of spine deformity. Therefore, different approaches have been developed aimed at achieving more accurate and objective screening results.

A scoliometer is a ruler-like handheld tool. It is an inclinometer to measure trunk asymmetry or axial trunk rotation (ATR) which is also known as rib hump deformity. The scoliometer provides a quantitative measurement to assess the degree of scoliosis. Different studies have found that the measurement from a scoliometer resulted in high intra-rater and inter-rater variations of ATR values and a high false positive rate. In addition, the scoliometer measurement does not correlate well with the Cobb method. Earlier studies have suggested that a scoliometer should not be exclusively used as a diagnostic tool.

Moire-fringe mapping is used to obtain the 3D shape of the back of a patient. Moire-fringes are generated by a grating projected on the target. The images of the fringes are captured by a video system. A contour line system and a sectional shape of the object are then automatically reconstructed and displayed on monitor by computer. Moire fringe mapping can produce very accurate data with a resolution up to 10 microns. Surfaces at a large angle are not measurable when the fringe density becomes too dense. In addition, the patient's position, body-build, and fat folds are other factors causing inaccuracy to the surface topography. Due to the lack of clinical experience on this technique, there is a poor correlation between the observed body and the underlying scoliosis.

Use of a quantec spinal image system is popular in the United Kingdom. The quantec spinal image system is based on Moire topography and raster-stereo photography. This system uses raster stereography to create an image of a fringe pattern and projected onto the patient's back. The system then produces a Q angle, a coronal plane measurement quantifying the coronal asymmetry reflected from the patient's images. However, this system is complex and relies on the surface topography that is a factor of inaccuracy. Photogrammetric method systems are based on laser scanning or photography technique. The laser scanning and video system offers a fast and accurate 3D measurement of scoliotic deformities which can be spatially recorded within a minute. The output of a digital 3D model provides a resolution up to 1 mm. Using this 3D model, spinal deformations information such as the Cobb angle is derived. These systems provide non-invasive and non-contact measurements. However, all of these techniques are based on the surface topography and none of them are portable or movable.

The Ortelius system developed by OrthoScan Technologies is a radiation-free spatial data capturing system to diagnose and monitor spinal deformities. During examination, the examiner palpates the patient's back to locate the spinous process of each vertebra and records the position of spinous process for all vertebrae using a 3D spatial sensor. The data can then be reconstructed into a computer model for calculating the spinal deformation indices. However, the position of transverse process cannot be obtained. The spinal column rotation cannot be considered. Moreover, the patient needs to be repeatedly palpated during the examination and the process may lead to a certain degree of discomfort. Even though the location of transverse processes are recorded by the 3D spatial sensor, it is manually determined by the operator based on body surface palpation, and this is subjective.

SUMMARY OF THE INVENTION

In a first preferred aspect, there is provided a three-dimensional (3D) ultrasound imaging system for assessing scoliosis. The system includes an ultrasound scanner to capture ultrasound images. The system also includes a spatial sensor to record the position and orientation of the captured ultrasound images. The system also includes a software module to mark features of vertebra in the captured ultrasound images, and the marked features are connected with lines in order to calculate angles and distances between the marked features for the calculation of the Cobb angle and spinal rotation angle based on the calculated angles and distances. The marked features are a reflection of the surfaces of the vertebra.

The software module may include an image enhancement module to enhance bony surface details in the captured images.

The software module may include an image marking module to identify captured images that contain marked features.

The software module may include an image magnifying module to magnify captured images for the identification of features of the vertebra.

The software module may include an image removal module to remove captured images that do not contain marked features.

The features of the vertebra may include edges, apexes of spinous and transverse processes.

The software module may include a virtual model generator to connect the marked features with lines to form a frame based skeleton virtual model of the spine. The virtual model generator may re-size and place corresponding vertebra segments in 3D space according to the features of the vertebra.

The ultrasound scanner may have a probe which is swiped over the back of a patient.

The probe may have a width of about 10 to 20 centimeters to enable scanning of all spinal processes in a single swipe.

The spatial sensor may comprise a transmitter and a receiver, and the receiver is operatively attached to the probe.

The spatial sensor may comprise a transmitter and a receiver, and the transmitter is operatively attached to the probe.

The system may further comprise a chest board.

The system may further comprise a height adjustable handrail to help a patient maintain a steady position.

In a second aspect, there is provided a method for assessing scoliosis. The method includes capturing ultrasound images. The method also includes recording the position and orientation of the captured ultrasound images. The method also includes marking features of vertebra in the captured ultrasound images, and the marked features are connected with lines in order to calculate angles and distances between the marked features for the calculation of the Cobb angle and spinal rotation angle based on the calculated angles and distances. The marked features are a reflection of the surfaces of the vertebra.

The method may further comprise enhancing bony surface details in the captured images.

The method may further comprise identifying captured images that contain marked features.

The method may further comprise magnifying captured images for the identification of features of the vertebra.

The method may further comprise removing captured images that do not contain marked features.

The method may further comprise forming a frame based skeleton virtual model of the spine using the lines connecting the marked features.

The method may further comprise re-sizing and placing corresponding vertebra segments in 3D space according to the features of the vertebra.

The method may further comprise displaying a projection image of marked features with the ultrasound images in 3D space.

The method may further comprise combining an X-ray projection image with the ultrasound images in 3D space.

In a third aspect, there is provided a computer-implemented method for automatically marking features of vertebra to assess scoliosis, the method comprising:

extracting bone reflection from a captured ultrasound image or removing all features of the image except the bone reflection by applying image processing; and
  locating the position of a bone in the image and marking the position with a marker;
  wherein the image processing includes any one from the group consisting of: maximum intensity reflection, maximum gradient, active contour, or image registration The method may further comprise discarding the image if no bone reflection is detected.

The method may further comprise analysing the location of markers for an identical process and detecting a peak of the process based on the 3D contour formed by the markers. The marker which corresponds to a feature of a vertebra with the smallest tissue depth is considered the peak of the process.

Advantageously, the 3D ultrasound system locates all spinous processes and also provides information relating to transverse processes. All processes that are located are in exact geometric order and dimension.

The present invention advantageously provides unlimited frequency of usage in assessment of scoliosis. On-site screening and mass screening for children is also made possible since no X-ray is necessary. The present invention provides long term monitoring for scoliosis treatment.

The present invention is safer and more accurate than traditional techniques of assessing scoliosis. The present invention is also cost effective because it does not require radiation specific equipment or highly skilled and experienced operators. The present invention is also compact and can fit in small clinic.

BRIEF DESCRIPTION OF THE DRAWINGS

An example of the invention will now be described with reference to the accompanying drawings, in which.

DETAILED DESCRIPTION OF THE DRAWINGS

Figure 1:
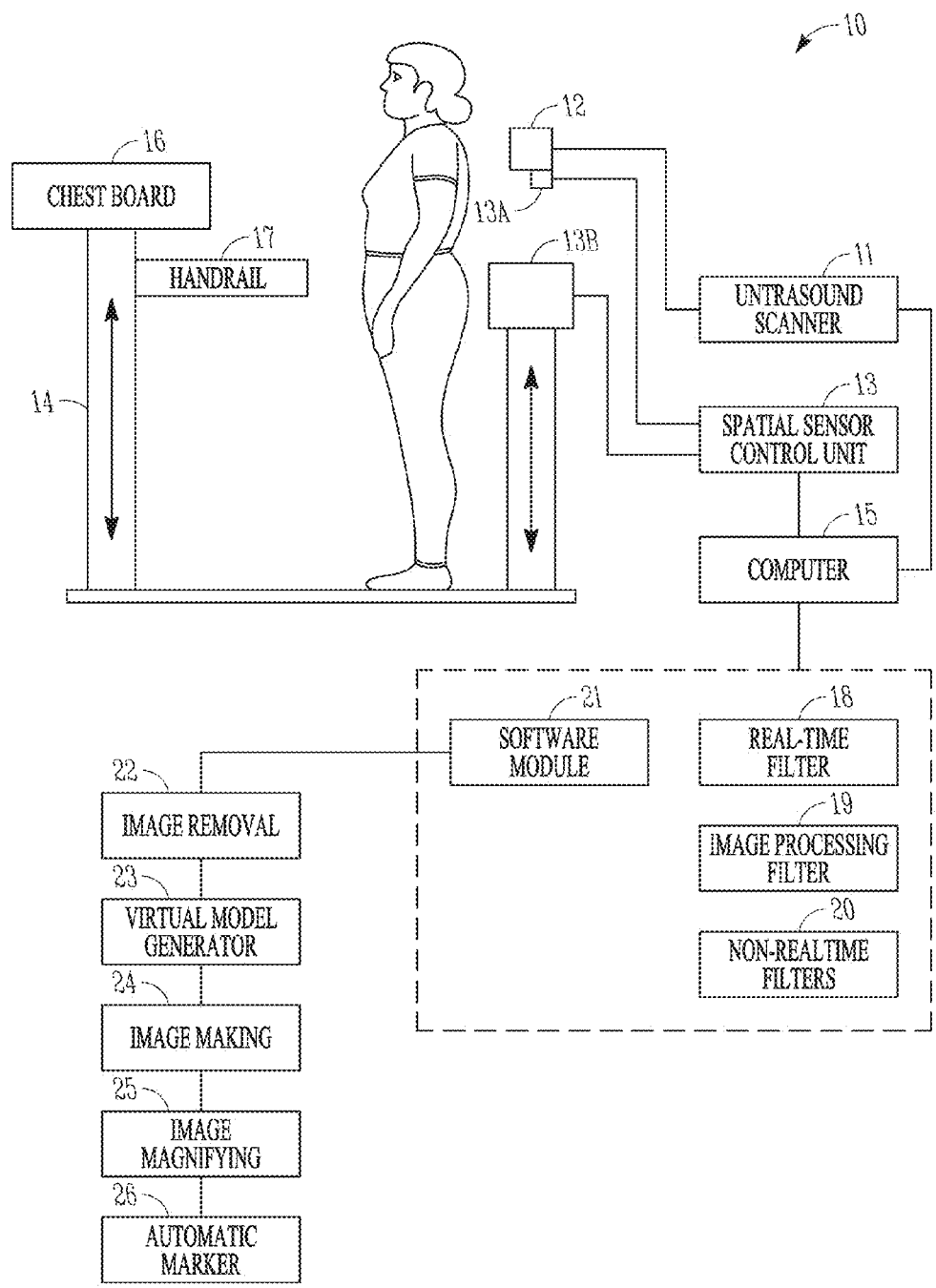
FIG. 1 is a block diagram of a 3D ultrasound system in accordance with an embodiment of the present invention.

Referring to FIG. 1, a 3D ultrasound system 10 for scoliosis assessment is provided. The system 10 generally comprises an ultrasound scanner 11 with an ultrasound brightness mode (US B-mode) probe 12, a 3D spatial sensor control unit 13, a framework 14, and a computer 15.

The framework 14 is adjustable in height and able to conveniently disassemble. A chest board 16 is operatively attached to the framework 14. The chest board 16 is a reference for the spatial sensor 13 which enables the physical distance between the chest board 16 and transmitter 13B of the spatial sensor 13 to be determined. The value of the distance is used to verify internal parameters for the calibration of the spatial sensor 13. Also, the chest board 16 provides a resting surface for the patient to lean on. During scanning with the probe 12, the patient may be moved forward by a force from the examiner. If this occurs, the chest board 16 helps to prevent the patient from moving forward too much and therefore minimise inaccuracies in the measurements taken. A handrail 17 is provided which may be operatively attached to the framework 14 to help the patient maintain a steady position during examination.

The ultrasound scanner 11 has a wide probe 12 (10 cm or above). This enables an examiner to obtain a set of spine images via a single swipe over the patient's spine. In contrast, the examiner needs to swipe two to three times with a normal probe (around 5 cm or less with width) to capture a complete set of images covering all spinous and transverse processes.

The system 10 measures the angle and dimension of spine using the spatial sensor 13 in true values instead of measuring from the projection of chest or spine X-ray film. This is more accurate because they are not relative values. The degree of spine rotation can also be obtained in the same examination. The spatial sensor control unit 13 is able to determine the position of probe 12 at any moment in time. The unit 13 consists of a small cube-shaped transmitter 13B and a tiny peanut size receiver 13A which is normally attached to the probe 12. Alternatively, the transmitter 13B may be operatively attached to the probe 12. The transmitter 13B generates a magnetic field in space. The receiver 13A senses the strength of magnetic field and the change of magnitude of the magnetic field. The results are processed by the spatial sensor control unit 13 to compute the position and orientation of the receiver 13A. The spatial information is sent to the computer 15 periodically. The position of the probe 12 is computed using a specific computational method and the spatial information. The computational method to obtain the position and orientation information of probe 12 and its generated B-mode image's pixels in the physical world, a series of rigid transforms are performed. Before this is done, the probe 12 must be calibrated to obtain a spatial and orientation relationship between the probe 12 and the receiver 13A. This is the first rigid transform matrix. Also, a second rigid transform matrix is defined which can be chosen in any position and orientation. This matrix is known as a system rigid transform. The spatial control unit 13 provides a final rigid transform matrix which defines the current position and orientation between the transmitter 13B and the receiver 13A. By multiplying these matrices, the position and orientation information of the probe 12 is obtained. Its B-mode image's pixels are obtained by multiplying the coordinate of pixels relative to the B-mode image.

Novel ultrasound scanning procedures, image processing techniques such as gaussian, sobel filtering, 3D virtualization methods such as OpenGL and Visualization Toolkit, and angle calculation approaches are used together to calculate the degree of spine's deformation in term of true distances and angles instead of an approximation or projected from a standard chest X-ray film. All pixels in the B-mode image can be transformed to a physical world location and orientation. If the distance is measured between two pixels in any B-mode images, the physical distance between the objects is obtained which are represented by these pixels. Similarly, the angle between two selected lines 42 is obtained, each of which can be defined by two pixels.

Figure 5:
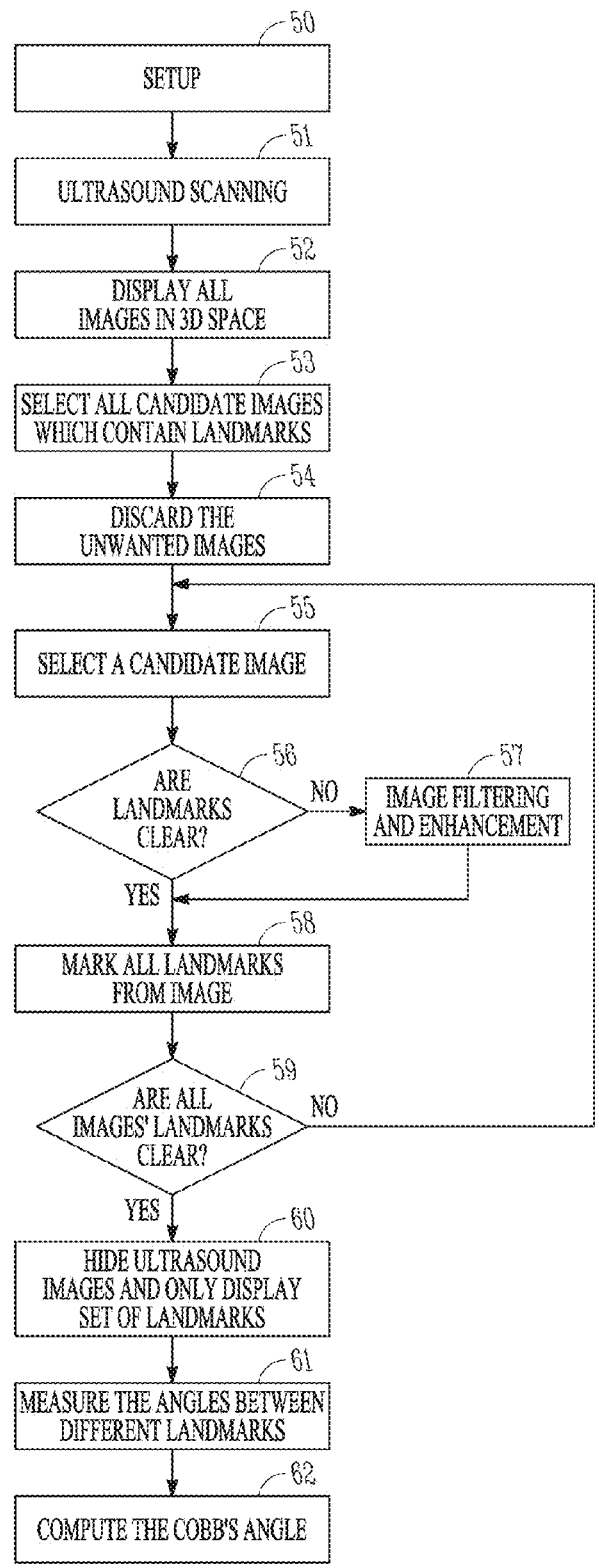
FIG. 5 is a process flow diagram of a method for scoliosis assessment in accordance with an embodiment of the present invention.

Referring to FIG. 5, the system 10 is set up (50) by deploying the framework 14 at a location and positioning the ultrasound scanner 11, spatial sensor 13 and computer 15. The patient is asked to stand in a proper position and is given instructions by the examiner. Ultrasound coupling gel or liquid is applied on the patient which covers the body area to be scanned. A gel pad or liquid bag can also be used to cover the body area and the ultrasound scanning can be conducted above the surface of the gel pad or liquid bag. This is particularly useful when the soft tissue layer covering the bone is very thin. The settings of the ultrasound scanner 13 are adjusted such as viewing depth, brightness, focus, gain, transmitting power, etc. The spatial sensor 13 is activated. B-mode images and corresponding spatial data are captured and then sent to the computer 15.

The patient's spine is scanned (51) with the B-mode probe 12 of the scanner 11 to capture ultrasound images. The scan commences from the L5 to T1 of the spine, or any selected portion of the spine. The scanning length may be shortened depending on the area of curvature. The total number of scanned images are around 500 to 1500. The patient is asked to stand still and hold the breath during the scanning process.

Figure 2:
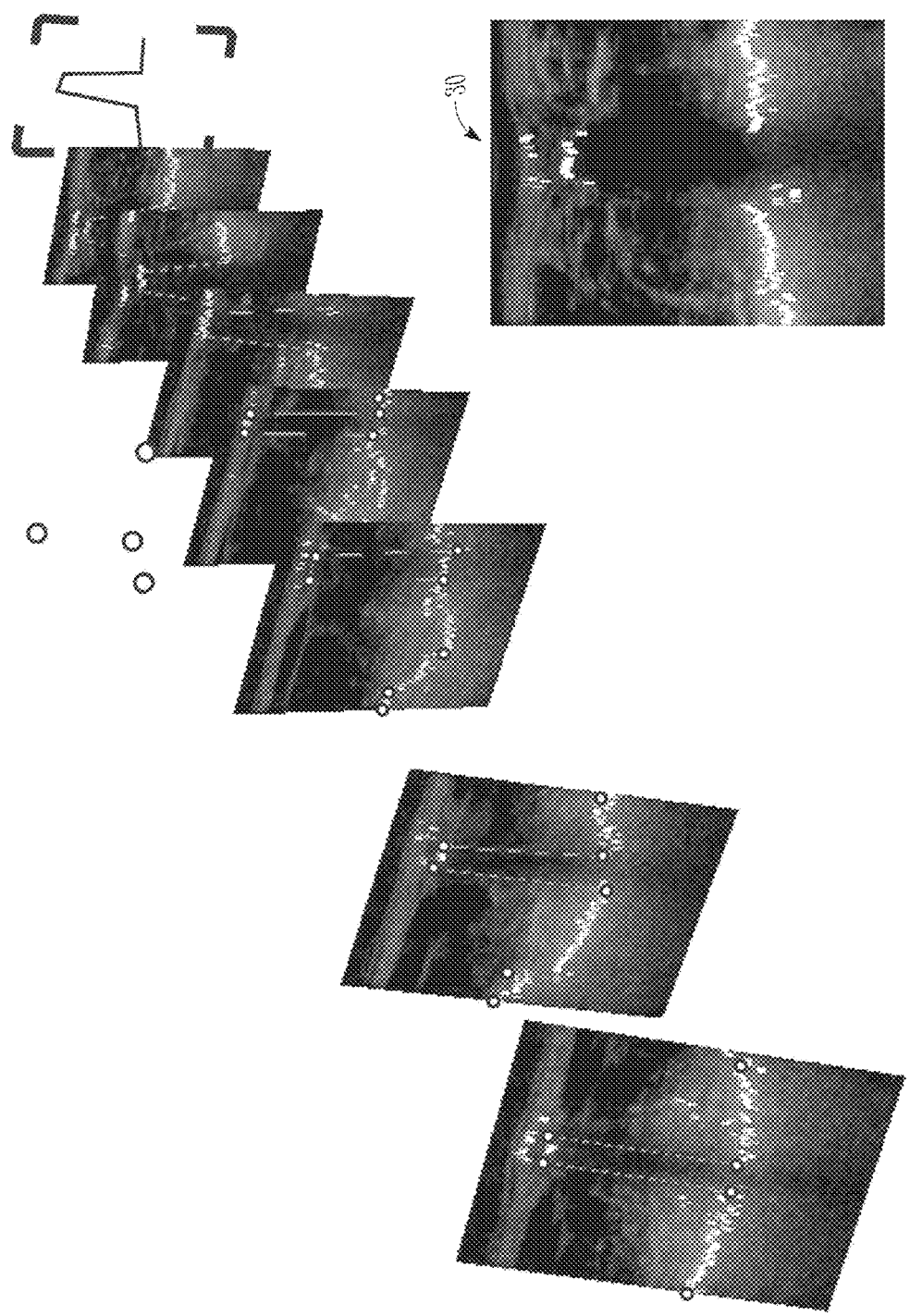
FIG. 2 is a set of ultrasound images captured by the system of FIG. 1 which are preprocessed to identify landmarks.

These captured images are processed by a software module 21 executing on the computer 15 via a video or USB interface in real-time. The images are displayed (52) in 3D space on the screen of the computer 15 in real-time as they are captured. The display of the captured images is depicted in FIG. 2. The images form a long image stack. The examiner performs a preliminarily check of the image consistency. If the images are fine, the patient may leave. Otherwise, the patient has to stand again for re-scanning.

Figure 6:
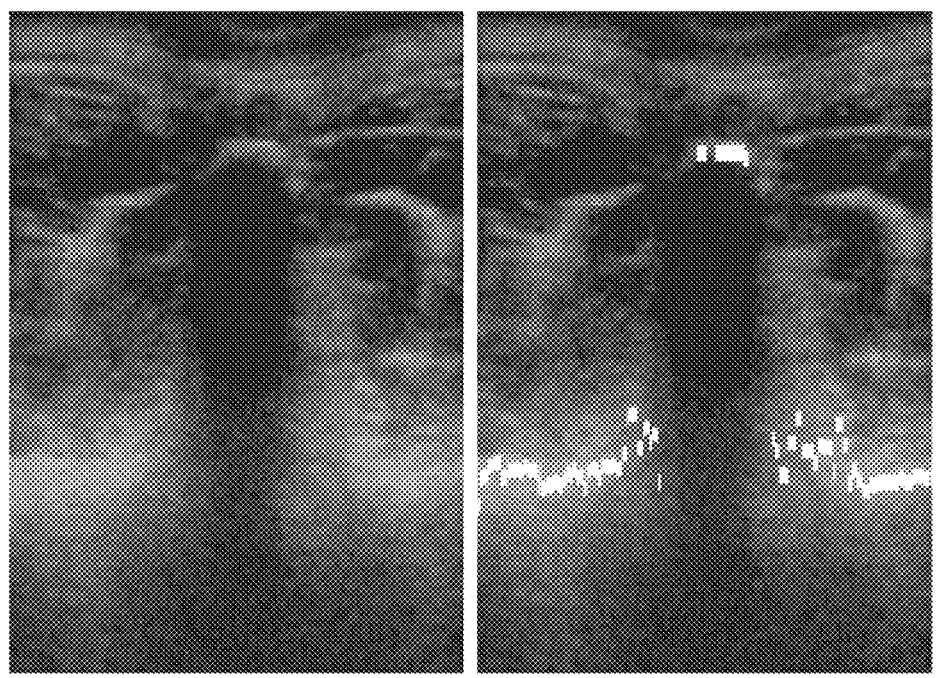
FIG. 6 is a set of two images, the left image is an original B-mode image and the right image is an enhanced image where the bone surface has been enhanced using a bone surface extraction filter.

The set of ultrasound images captured may be preprocessed by various kinds of image processing filters 19. In order to enhance the bony surfaces of the vertebra in the ultrasound images, a real-time filter 18 is used on the images. The real-time filter 18 enhances the bony surface in the image and the enhanced images guide the examiner to easily move the probe 12 to make the vertebrae locate in a proper position in the image. The left image in FIG. 6 is the original ultrasound image and the right image in FIG. 6 is the left image which has been enhanced by the real-time filter 18. The real-time filter 18 extracts useful bone shape by enhancing the maximum or gradient change of pixels in the vertical direction (A-mode direction). Furthermore, pseudo color coding can be used to enhance the visualization of the vertebrae, with the bone interface highlighted with a selected color and other regions represented in grey levels. These enhancements enable easier identification of landmarks during image capture. For example, the shape of the vertebra in FIG. 6 can then be identified by manual or automatic marking procedures to find the apex of spinous process and transverse processes of an individual image.

Automatic marking procedures may be performed by the computer 15 via an automatic marker module 26 of the software module 21. The automatic marker module 26 extracts the bone (the surfaces of the vertebra) reflection from the image or removes all feature of the image except the bone reflection using image processing techniques. These image processing techniques include maximum intensity reflection, maximum gradient, active contour, or image registration. The automatic marker module 26 is then able to locate the position of bone and automatically mark them. If no bone reflection is detected in an image, the image is discarded because there is no useful information in this image. After the images without landmarks are discarded, one spinal process may still correspond to a series of images. The location of the landmarks in different images for the same process is analyzed and the peak of the process is automatically detected based on the 3D contour formed by the landmarks. One approach is to use the depth of the landmarks as a criteria. The landmark with the smallest tissue depth is the peak of the process. After the processes for all vertebrae are obtained, the Cobb angle and rotational angle are automatically calculated as later described.

Captured images which contain landmarks are selected (53). These are referred to as candidate images because they are images which contain at least one landmark. Candidate images which potentially contain landmarks are selected by viewing the image stack. The user can use a computer mouse to navigate the image stack freely on the computer screen. The selected candidate image is enlarged for a better view by the examiner which can be displayed where the image is or in a separated location as depicted by the image 30 shown the bottom right corner in FIG. 2. If the examiner finds a candidate image, it may be picked from the image stack by clicking it. The selected candidate image is highlighted. The user can repeat the process until all candidate images have been found in the image stack. However, if the user finds difficulty in locating the candidate images from navigating the image stack alone, tools are designed to help viewing the image stack such as volume slice, re-slice, and preview plane. Nevertheless, the user can discard the unselected images in the image stack.

Figure 7:
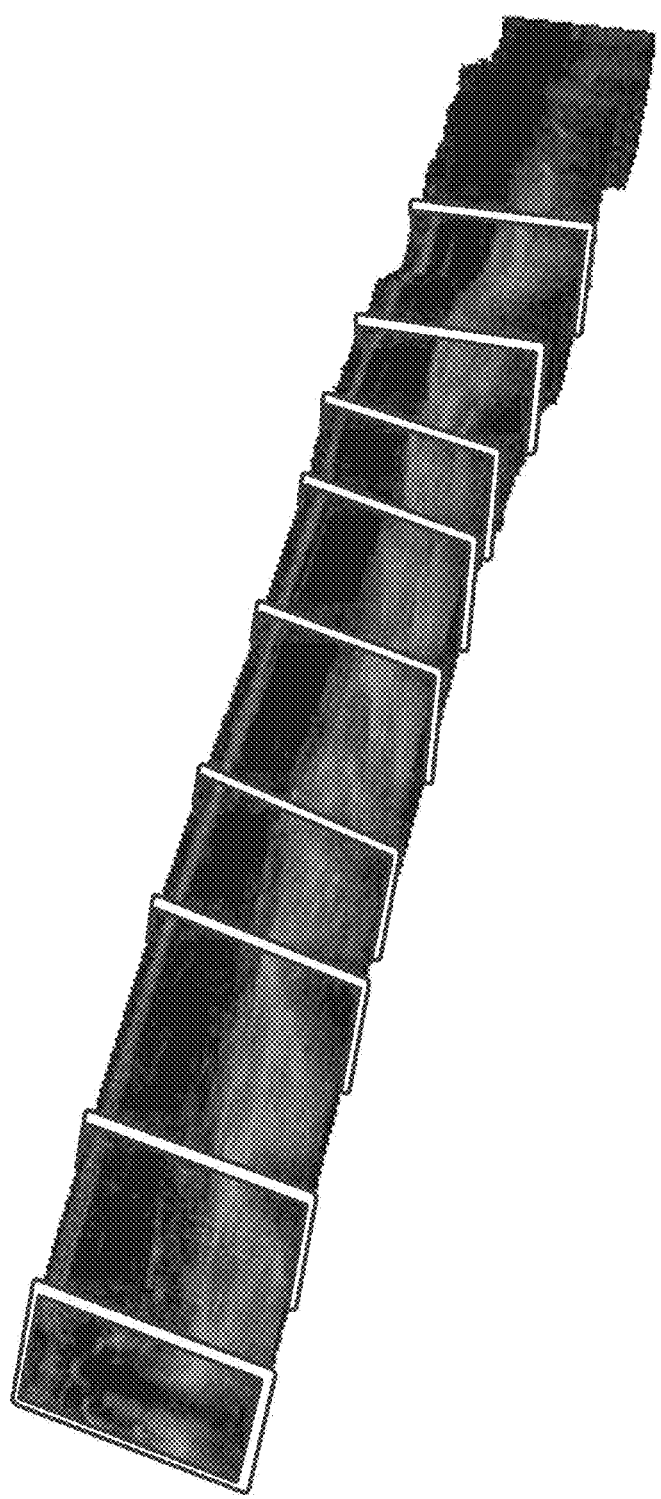
FIG. 7 is a selection of all candidate images from an original image set captured by the system of FIG. 1.

Captured images without landmarks are discarded (54) to save on storage space. Candidate images potentially containing a vertebra apex or landmark are saved to disk. Therefore, the size of useful data is minimized and the operational speed of the system 10 improves. The set of images initially captured by the scanner 11 is very large in size because they are high resolution images. The images without landmarks are removed by an image removal module 22 of the software module 21. What remains are the images containing the landmarks as depicted in FIG. 7.

Figure 3:
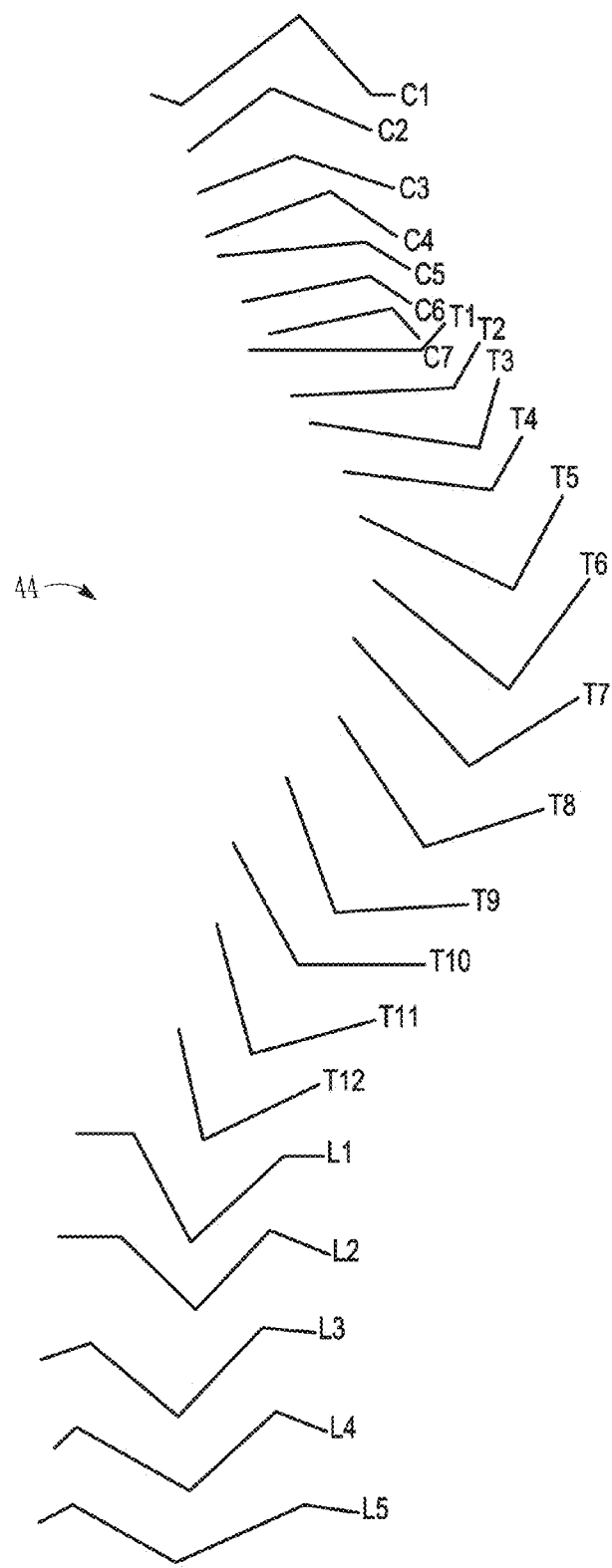
FIG. 3 is a virtual model of a patient's spine formed from the identified landmarks of FIG. 2.

Each of the candidate images is selected (55). The landmarks in the image are identified and marked by markers 41 as depicted in FIG. 3. The landmarks represent the important features of vertebra including edges, spinous and transverse processes. Each vertebra such as c1, c2, c3, etc may contain multiple landmarks usually from two to five landmarks. The system 10 requires about two or three landmarks from each vertebra for the purpose of generating the virtual model 44. The landmarks that are marked in the system 10 correlate to actual bone surfaces. The actual physical position of the landmark is known from the information provided by the spatial sensor 13. Knowing the actual physical position enables an accurate virtual model 44 to be constructed for the spine geometrical structure. Both the Cobb angle and angle of rotation of the spine are accurately measured at the same time based on the virtual model 44.

Figure 8:
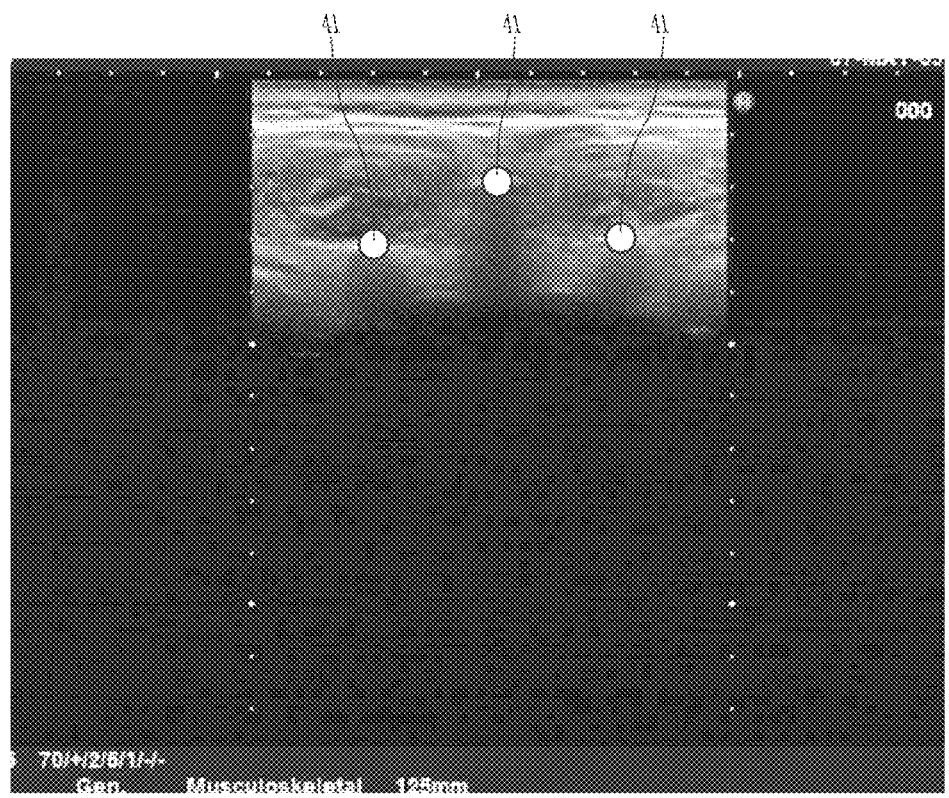
FIG. 8 is a B-mode image showing a vertebrae with markers placed on apex.

The examiner must determine (56) if the landmarks that are marked are visually clear. If they are not, a different imaging method is used to enhance the quality of image and manifest the landmarks. Various non-real-time filters 20 can also be used further to enhance the apexes in the image. Referring to FIG. 8, in some images, these apexes are very obvious which makes it unnecessary to perform any non-real-time filtering 20. If a filter is applied (57), the computer 15 enhances the image and the landmarks. Filters such as brightness filter, contrast filter and edge filter can be used for enhancing the quality of an individual image or all candidate images. The filtering process is repeated until a desirable image is obtained.

Figure 9:
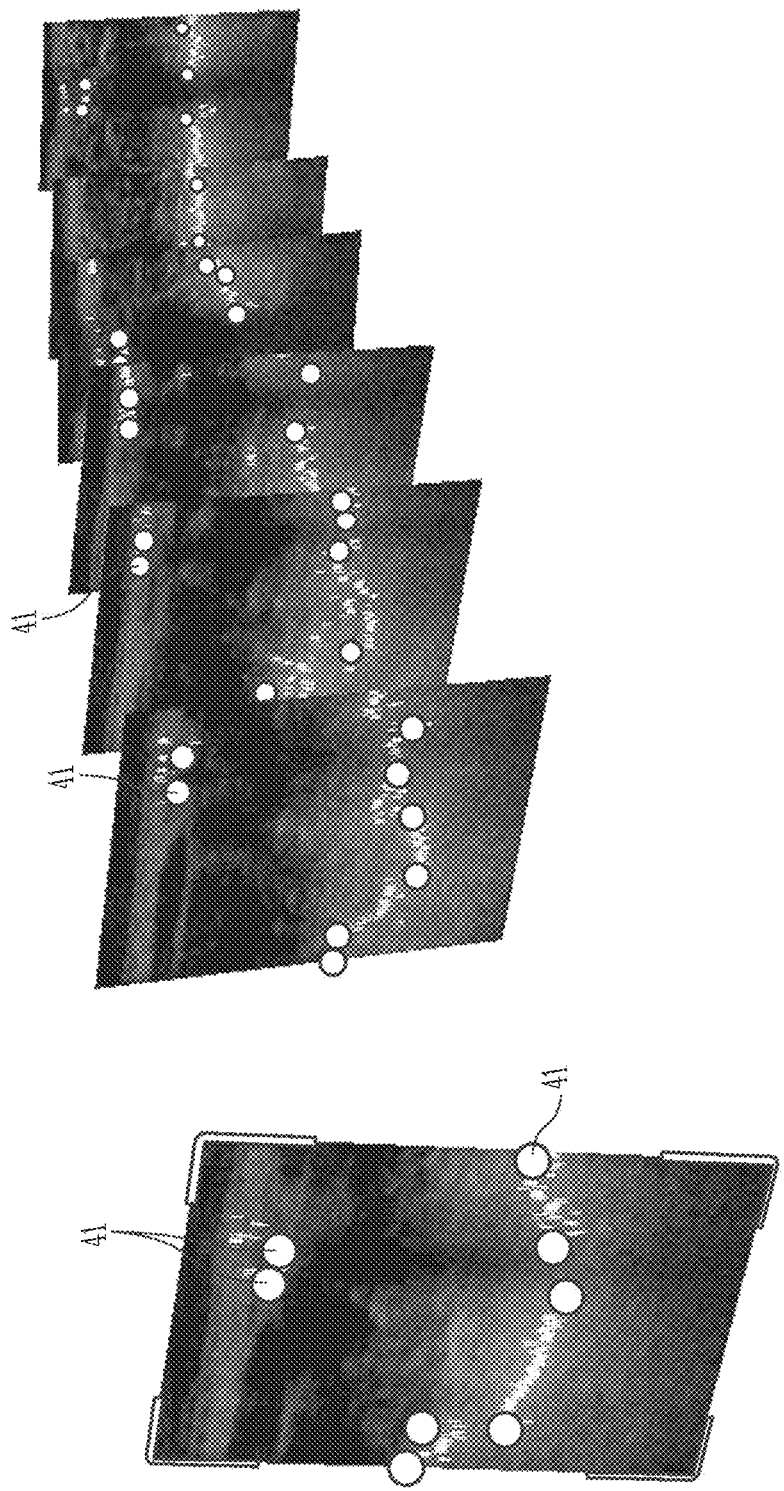
FIG. 9 is a sequence of images with landmarks that have been marked on the images.

Landmarks are marked (58) by the examiner selecting the image landmark indicator on the computer 15. Then, a sphere or a marker 41 of any shape is placed onto the landmark in the 3D position. This step is repeated until all landmarks in the image are found. The sphere 41 indicates the position and existence of the landmark in the image. Referring to FIG. 9, all candidate images are marked with landmarks. In some cases, one spinal process can be viewed in a series of images. In these cases, a representative image can be selected, such as the one in the middle of that series, or a local volume image can be formed and the peak of the process can be identified in the local volume image. An image marking module 24 of the software module 21 allows examiners to identify images that contain markers 41. The software module 21 also includes an image magnifying module 25 to assist examiners in identifying landmarks during image marking.

When all the landmarks from all the selected images have been marked (59), they are displayed on the screen of the computer. This ensures all processes from spine have been found.

Figure 4:
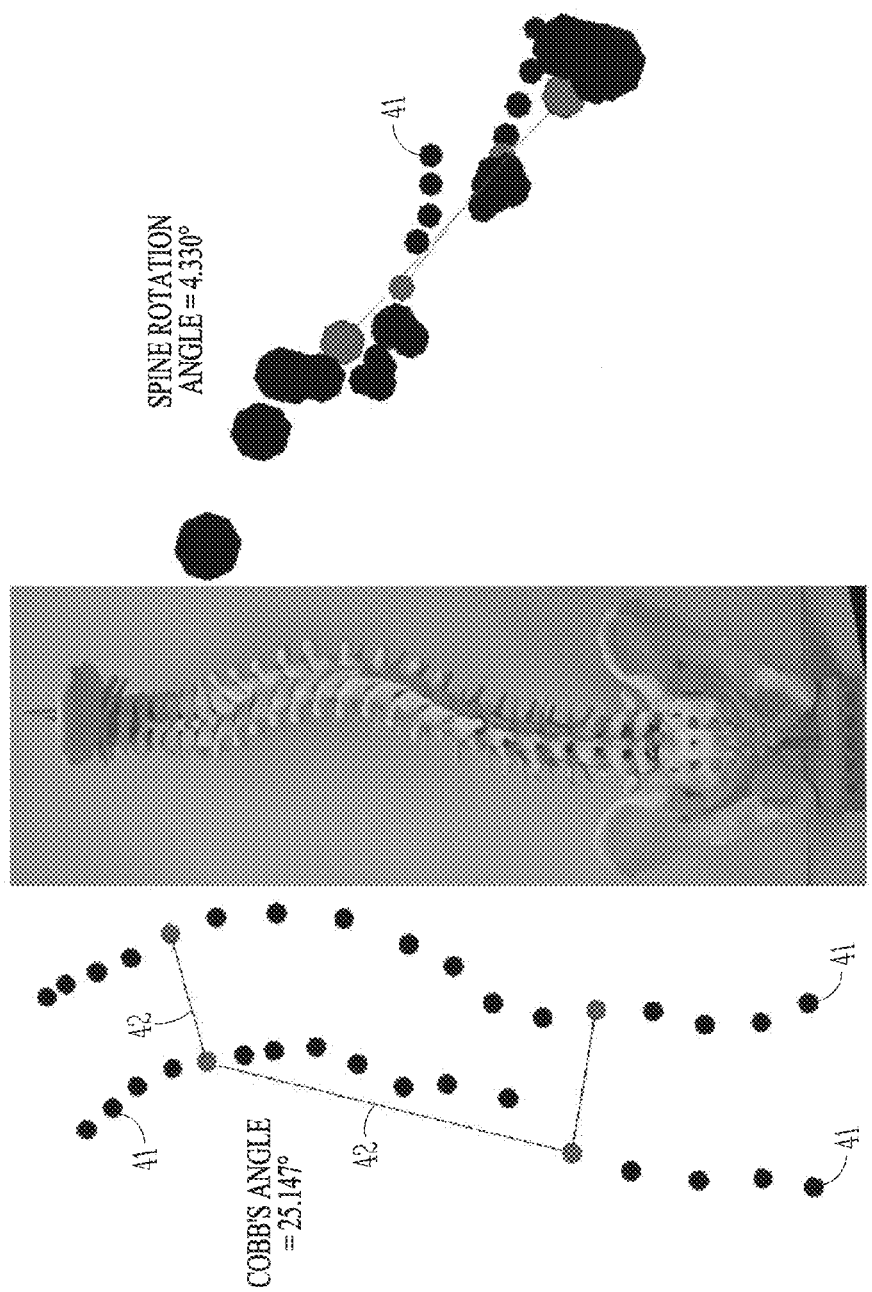
FIG. 4 is a final result generated by the system of FIG. 1 showing the Cobb angle, spine rotation and angle and image of the patient's spine.
Figure 10:
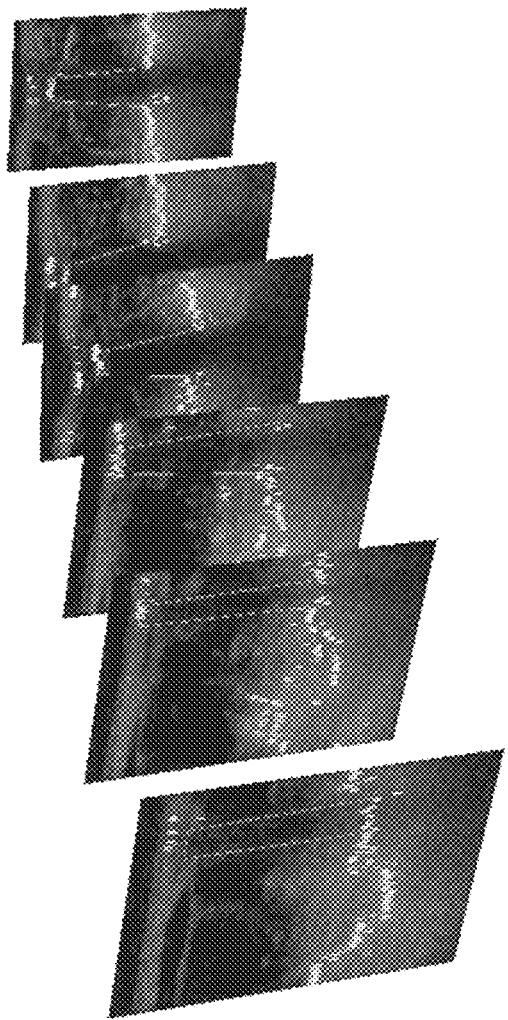
FIG. 10 is a sequence of images with lines connecting the landmarks within one image.
Figure 10:
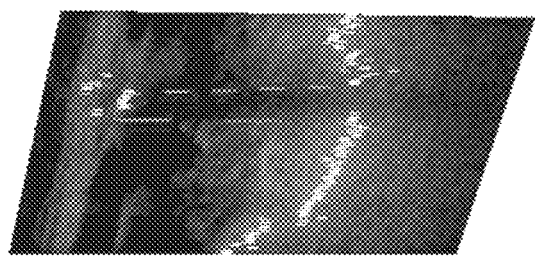

The image stack is hidden (60) so that only the markers 41 are displayed. The markers 41 in the image are connected with lines 42 to form a frame based skeleton virtual model 44 of the spine using a virtual model generator 23 of the software module 21 as depicted in FIGS. 3, 4 and 10. By hiding the B-mode images, all landmarks are exposed inside a virtual 3D space and seen easily by the examiner. The landmarks from the same B-mode image are connected in sequence with lines 42. The lines 42 and markers 41 become a frame-based skeleton virtual model 44 of the patient's spine. Since, the actual dimensions and angles are obtained by the spatial sensor and calculations. All landmarks pose into their exact positions. The distance between landmarks and the angles between lines 42 formed by landmarks can then be measured based on the spatial information of each selected landmarks. The Cobb angle can then be calculated manually or automatically. Furthermore, the information of the markers 41 can be used to re-size and place corresponding virtual vertebra segments on the 3D space to enhance the visualization. The virtual model generator 23 may use this information to re-size and place corresponding vertebra segments in 3D space.

Angles among the landmarks are measured (61) by the examiner clicking pairs of landmarks from different vertebras with maximum tilt difference. This process can be performed automatically by the computer 15 if necessary.

The Cobb angle is the angle formed between a line drawn parallel to the superior endplate of one vertebra above the fracture and a line drawn parallel to the inferior endplate of the vertebra one level below the fracture. The Cobb angle is computed (62) from the maximum tilt angles among the pairs of landmarks. Since, the Cobb angle is defined as the projection of spine curve angle from the sagittal plane; the angle still needs to be computed and projected onto a fixed plane before the Cobb angle can be computed. The landmarks of transverse processes from the same vertebrae which are the two most tilted vertebrae from different ends of the spine are connected to form a 3D vector line. Similarly, the vector is obtained by connecting the landmarks of transverse processes from the other most tilted vertebrae from other end of the spine. This is depicted in FIG. 4. These 3D vector lines 42 are then projected onto the sagittal plane. The newly formed projected vector lines 42 can then be used to compute the angle between them by vector dot product. The angle obtained is equivalent to the Cobb angle if it was obtained from a chest X-ray. When the Cobb angle has been computed it is displayed to the examiner as depicted in FIG. 4 together with the spine rotation and angle and virtual model 44 of the patient's spine.

Since the system 10 does not require harmful radiation to operate, it can be used for any patient without limitation on time or frequency. The system 10 is a radiation free system which means that it does not require a radiation safe room, expensive X-ray equipment or certified X-ray technician. The initial cost and operational cost is dramatically reduced for scoliosis assessment.

The system 10 is not restricted in the place or time it must be used. Therefore, the rate of usage is increased and enables on-site and mass screening. The operation of the system 10 in a small and non-radiation safe room becomes viable using the system 10. This is because the ultrasound scanner 11 and spatial sensor 13 are small enough to be moved around or carried by hand. The framework 14 can also be assembled and disassembled so as to move into compact room. It is safe to operate by any trained staff at any place.

To handle a vast amount of ultrasound images, a faster graphical card, faster and multi-core based processor, and more memory provides an improvement in performance.

Figure 11:
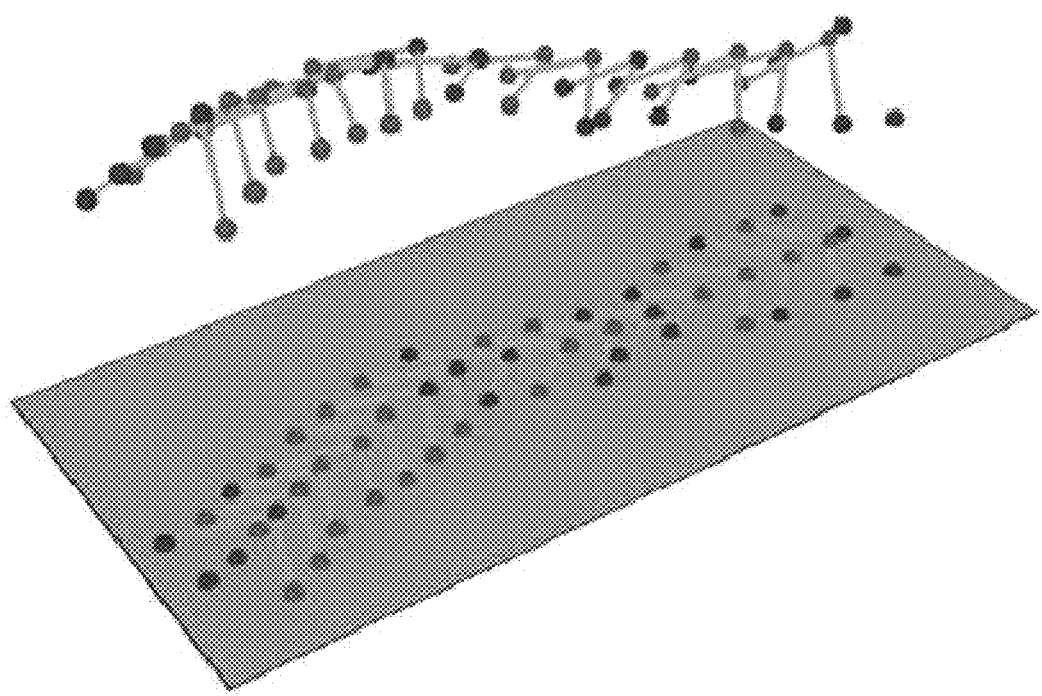
FIG. 11 is a set of projection images with marked features in 3D space.
Figure 12:
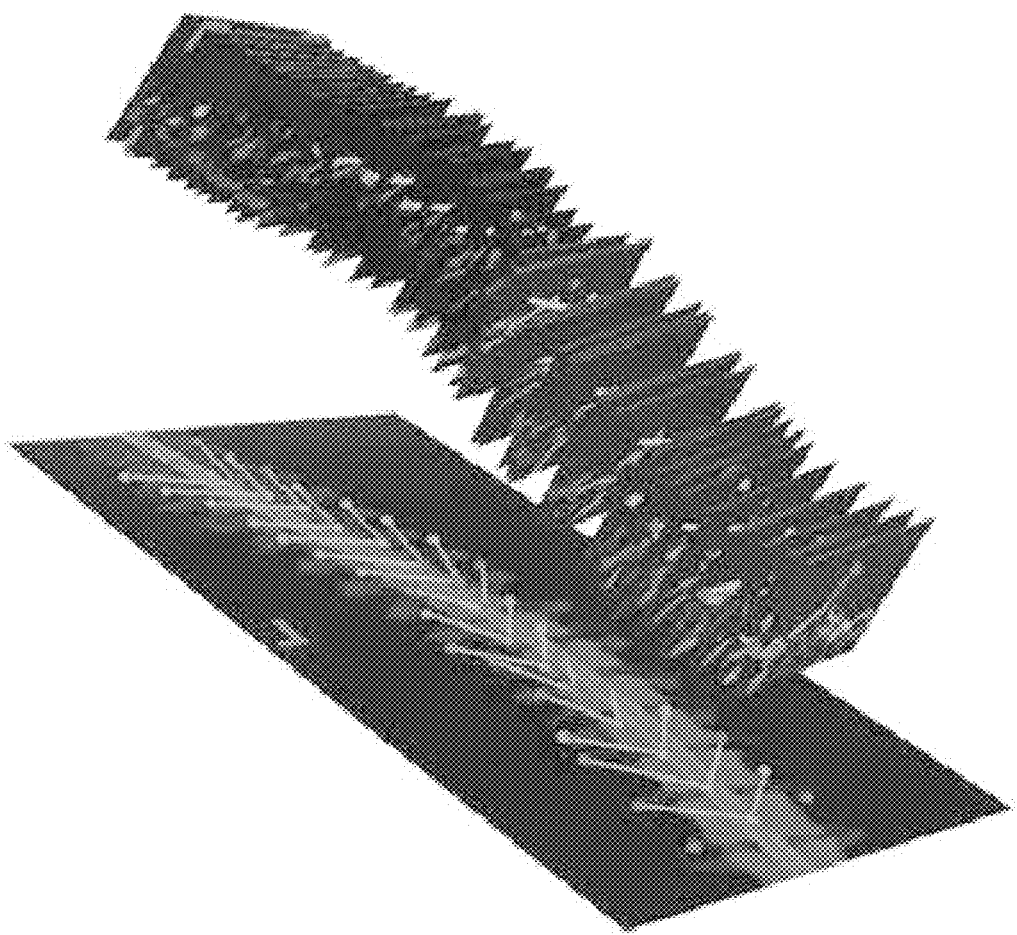
FIG. 12 is a set of projection images along side ultrasound images.

Referring to FIGS. 11 and 12, it may be very useful to view a projection X-ray image together with the landmarks of the original captured ultrasound images in 3D space. Since a traditional X-ray assessment only provides a projection image, the system 10 may receive greater acceptance from experienced examiners if it can also provide a projection image. Both X-ray assessment and the system 10 may be used together where the system 10 is frequently used for long term studies. Therefore, the system 10 has the ability to view a projection image of marked features together with the ultrasound images. Furthermore, the system 10 has the ability for X-ray images to be fused or combined together with the ultrasound measurement.

Although scoliosis has been described, the invention is applicable for assessing the outcome of hand therapy/bone setting or physical therapy provided by a traditional Chinese medicine practitioner. The 3D ultrasound imaging system 10 offers a tool to potentially measure different kinds of musculoskeletal structures.

Although an electromagnetic spatial sensor has been described, it is envisaged that other types of spatial sensing techniques may be used. These include: marker tracking using an optical visible or infrared camera, acoustic locating, and mechanical spatial locating using multiple articulating joints, etc.

Although the drawings are in black and white, actual images on the computer screen include colour for easier identification of landmarks and calculated information.

Monthly, weekly, or daily assessment of scoliosis is possible. A continuous monitoring of the outcome during treatment for scoliosis is very important. By contrast, the standard X-ray assessment limits the time between consecutive assessments from 3 to 9 months, because of the radiation hazard.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

We claim:

1. A three-dimensional (3D) ultrasound imaging system for assessing scoliosis, the system comprising:
    an ultrasound scanner to capture a set of B-mode ultrasound images wherein each image of the set includes a plurality of pixels corresponding to features of a vertebra;
    a spatial sensor to record the position of each captured ultrasound image of the set and to record the orientation of each captured ultrasound image of the set; and
    a computer comprising a software module configured to enhance, on an individual basis, each captured ultrasound image of the set and to mark features of vertebra in selected ultrasound images of the set, and to connect the marked features with lines for calculating angles and distances between the marked features for calculating the Cobb angle and spinal rotation angle based on the calculated angles and distances;
    wherein the marked features are a reflection of the surfaces of the vertebra and wherein a marked feature corresponds to a peak of a spinous process or a transverse process, detected based on a 3D contour formed by the marked features.

2. The system according to claim 1, wherein the software module includes an image enhancement module to enhance bony surface details in the selected ultrasound images.

3. The system according to claim 1, wherein the software module includes an image marking module to identify captured images that contain marked features.

4. The system according to claim 1, wherein the software module includes an image magnifying module to magnify captured images for the identification of features of the vertebra.

5. The system according to claim 1, wherein the software module includes an image removal module to remove captured images that do not contain marked features.

6. The system according to claim 1, wherein the features of the vertebra include edges, apexes of spinous processes, and apexes of transverse processes.

7. The system according to claim 1, wherein the software module includes a virtual model generator to connect the marked features with lines to form a frame based skeleton virtual model of the spine.

8. The system according to claim 7, wherein the virtual model generator re-sizes and places vertebra segments of the vertebra in 3D space according to the marked features of the vertebra.

9. The system according to claim 1, wherein the ultrasound scanner has a probe which is swiped over the back of a patient.

10. The system according to claim 9, wherein the probe has a width of about 10 to 20 centimeters to enable scanning of all spinal processes in a single swipe.

11. The system according to claim 9, wherein the spatial sensor comprises a transmitter and a receiver, and the receiver is operatively attached to the probe.

12. The system according to claim 9, wherein the spatial sensor comprises a transmitter and a receiver, and the transmitter is operatively attached to the probe.

13. The system according to claim 1, further comprising a chest board.

14. The system according to claim 1, further comprising a height adjustable handrail to help a patient maintain a steady position.

15. The system of claim 1 wherein the software module is configured to perform a computer-implemented method comprising:
    extracting bone reflection from a captured ultrasound image or removing all features of the image except the bone reflection by applying image processing; and
    locating the position of a bone in the image and marking the position with a marker;
    wherein the image processing includes any one from the group consisting of: maximum intensity reflection, maximum gradient, active contour, or image registration.

16. The system of claim 15, wherein the software module is configured to discard the image if no bone reflection is detected.

17. A method for assessing scoliosis, the method comprising:
    capturing a set of B-mode ultrasound images wherein each image of the set includes a plurality of pixels corresponding to features of a vertebra;
    recording the position of each captured ultrasound image of the set and recording the orientation of each captured ultrasound image of the set; and
    enhancing, on an individual basis, each captured ultrasound image of the set and marking features of vertebra in selected ultrasound images of the set, and connecting the marked features with lines for calculating angles and distances between the marked features;
    calculating the Cobb angle and spinal rotation angle based on the calculated angles and distances;

wherein the marked features are a reflection of the surfaces of the vertebra and wherein a marked feature corresponds to a peak of a spinous process or a transverse process, detected based on a 3D contour formed by the marked features.

18. The method according to claim 17, further comprising enhancing bony surface details in the selected ultrasound images.

19. The method according to claim 17, further comprising identifying captured images that contain marked features.

20. The method according to claim 17, further comprising magnifying captured images for the identification of features of the vertebra.

21. The method according to claim 17, further comprising removing captured images that do not contain marked features.

22. The method according to claim 17, further comprising forming a frame based skeleton virtual model of the spine using the lines connecting the marked features.

23. The method according to claim 17, further comprising re-sizing and placing vertebra segments of the vertebra in 3D space according to the marked features of the vertebra.

24. The method according to claim 17, further comprising displaying a projection image of marked features with the ultrasound images in 3D space.

25. The method according to claim 17, further comprising combining an X-ray projection image with the ultrasound images in 3D space.

* * * * *